United States Patent
Elliott

(10) Patent No.: US 7,458,937 B2
(45) Date of Patent: Dec. 2, 2008

(54) METHOD AND SYSTEM FOR ASSESSING BREATHING EFFECTIVENESS VIA ASSESSMENT OF THE DYNAMIC ARTERIAL PRESSURE WAVE USING THE OSCILLOMETRIC MEASUREMENT TECHNIQUE

(75) Inventor: Stephen Bennett Elliott, Allen, TX (US)

(73) Assignee: Coherence LLC, Allen, TX (US)

( * ) Notice: Subject to any disclaimer, the term of this patent is extended or adjusted under 35 U.S.C. 154(b) by 272 days.

(21) Appl. No.: 11/032,662

(22) Filed: Jan. 11, 2005

(65) Prior Publication Data

US 2006/0155167 A1      Jul. 13, 2006

(51) Int. Cl.
*A61B 5/00* (2006.01)
*A61B 5/02* (2006.01)
(52) U.S. Cl. ............... 600/485; 600/503; 600/529
(58) Field of Classification Search ............... None
See application file for complete search history.

(56) References Cited

U.S. PATENT DOCUMENTS

| | | | |
|---|---|---|---|
| 5,997,482 A * | 12/1999 | Vaschillo et al. | 600/484 |
| 6,212,135 B1 | 4/2001 | Schreiber | |
| 6,301,499 B1 | 10/2001 | Carlson et al. | |
| 6,616,613 B1 * | 9/2003 | Goodman | 600/504 |
| 6,656,116 B2 * | 12/2003 | Kim et al. | 600/300 |
| 7,117,032 B2 * | 10/2006 | Childre et al. | 600/545 |
| 7,163,512 B1 | 1/2007 | Childre et al. | |
| 7,255,672 B2 | 8/2007 | Elliott | |
| 2004/0260186 A1 * | 12/2004 | Dekker | 600/483 |
| 2005/0096555 A1 | 5/2005 | Elliott | |
| 2005/0209503 A1 | 9/2005 | Elliott | |
| 2005/0288601 A1 * | 12/2005 | Wood et al. | 600/513 |
| 2007/0056582 A1 | 3/2007 | Wood et al. | |
| 2007/0173684 A1 | 7/2007 | Elliott | |

OTHER PUBLICATIONS

StressEraser, http://www.stresseraser.com homepage, downloaded Oct. 11, 2007, 4 pages.

* cited by examiner

*Primary Examiner*—Robert L Nasser
(74) *Attorney, Agent, or Firm*—Winthrow & Terranova, PLLC

(57) ABSTRACT

The present invention specifies a method and system for assessing breathing effectiveness via dynamic assessment of respiratory sinus arrhythmia and the consequent arterial pressure wave using the oscillometric measurement technique. Arterial pressure wave peak pressure, valley pressure, amplitude, and rate are characterized and displayed for diagnostic and remedial purposes. The dynamic change in respiratory sinus arrhythmia and resultant arterial pressure wave is visually presented in real time as user biofeedback. A respiratory sinus arrhythmia generator generates varying frequencies to which the user synchronizes their breathing cycle for purposes of increasing arterial pressure wave amplitude with a consequent increase in breathing depth and decrease in breathing frequency. An instructive method in the application of the present invention is also specified.

30 Claims, 12 Drawing Sheets

| RSA Signal Generator Setting (Breathing Cycles per Minute) | Numeric Value | Frequency of Oscillation (sec) |
|---|---|---|
| 5 | 18 | 12 |
| 6 | 16 | 10 |
| 7 | 14 | 9 |
| 8 | 12 | 8 |
| 9 | 19 | 7 |
| 10 | 8 | 6 |
| 15 | 6 | 4 |
| 20 | 4 | 3 |
| 30 | 2 | 2 |

| Input Arterial Pressure Wave Amplitude | Numeric Value |
|---|---|
| 70 | 18 |
| 60 | 16 |
| 50 | 14 |
| 40 | 12 |
| 30 | 10 |
| 20 | 8 |
| 5 | 6 |
| 3 | 4 |
| 1 | 2 |

FIGURE 13

METHOD AND SYSTEM FOR ASSESSING BREATHING EFFECTIVENESS VIA ASSESSMENT OF THE DYNAMIC ARTERIAL PRESSURE WAVE USING THE OSCILLOMETRIC MEASUREMENT TECHNIQUE

RELATED PATENT FILINGS

Method and System for Consciously Synchronizing the Breathing Cycle with the Natural Heart Rate Cycle (Ser. No. 10/699,025), System and Method for Synchronizing the Heart Rate Variability Cycle With The Breathing Cycle (Feb. 19, 2004), Method of Presenting Audible and Visual Cues for Synchronizing the Breathing Cycle With An External Timing Reference for Purposes of Synchronizing The Heart Rate Variability Cycle With The Breathing Cycle (Mar. 15, 2004), Method and System Providing A Fundamental Musical Interval for Heart Rate Variability Synchronization (Mar. 23, 2004), Method and System of Respiratory Therapy Employing Heart Rate Variability Coherence (Ser. No. 10/814,035), Method and System of Breathing Therapy for Reducing Sympathetic Predominance With Consequent Positive Modification of Hypertension (Ser. No. 10/932,636)

FIELD OF THE INVENTION

The present invention relates to the field of human health and in particular to the field of "arterial pressure wave" assessment. This form of assessment is related to but different from traditional "blood pressure" measurement.

BACKGROUND OF THE INVENTION

Per the present state of the art, for practical purposes, noninvasive blood pressure is measured in one of two primary ways. The first method is the ascultatory method wherein blood flow in the brachial artery is impeded via a pressure cuff and "listened to" for purposes of assessing the state of the flow or lack thereof and consequent pressures relating to cardiac systole and diastole.

The second primary method is the oscillometric method wherein a pressure cuff is applied and the variation of pressure oscillations in the cuff are used to determine systolic and diastolic pressure. Due to limitations with each method, the ascultatory and oscillometric methods are sometimes used in combination to maximize accuracy.

Even so, per the present state of the art, neither the ascultatory method, nor the oscillometric method, nor their use in combination is adequately complete for purposes of assessing the comprehensive status of arterial pressure and patient health. This is because neither adequately address characterization of the arterial pressure wave resulting, or not, from respiratory sinus arrhythmia. By and large, both auscultatory and oscillometric assessment methods assume that the heartbeat rate varies little, where, in reality, the heart beat rate and resultant background arterial pressure can and should vary widely. This should-be wide variation is due to the phenomenon of respiratory sinus arrhythmia (RSA), this being the fact that the heartbeat tends to increase coincident with inhalation and decrease coincident with exhalation. Respiratory sinus arrhythmia gives rise to the phenomenon known as the "arterial pressure wave" which rises and falls with respiration. The arterial pressure wave is a well recognized physiological phenomenon, "With each cycle of respiration, the arterial pressure usually rises and falls 4 to 6 mm Hg in a wavelike manner, giving rise to so-called respiratory waves in the arterial pressure. During deep respiration, the blood pressure can rise and fall as much as 20 mm Hg with each respiratory cycle." (Medical Physiology—Guyton and Hall, 2000) Because, diastolic pressure is highly related to respiratory sinus arrhythmia, under ideal breathing circumstances, this author (Elliott) has measured systolic and diastolic pressures that differ by as much as 70 mm Hg. and diastolic pressures less than 50 mmHg, diastolic pressure being particularly affected by robust respiratory sinus arrhythmia. Fundamentally, the arterial pressure wave is a consequence of increasing heartbeat rate and heart output coincident with inhalation and a decreasing heartbeat rate and output coincident with exhalation.

When a human subject is breathing in a relatively rapid and shallow manner, as do most people when in the state of rest or semi-activity, their heartbeat varies only slightly between its upper and lower limits, for example 81-86 beats per minute as depicted in FIG. 1. Relatively rapid shallow breathing results in a minimal arterial pressure wave and for this reason a relatively small variation in pulse pressure as assessed by oscillometric measurement as depicted in FIG. 2. Under these circumstances, present ascultatory and oscillometric methods yield approximately the same measurement result.

In the case where breathing is properly slow and deep, the heartbeat rate tends to vary to a much wider degree, for example 60-96 beats per minute as depicted in FIG. 3. A widely varying heart rate variability results in a widely varying arterial pressure wave which results in a widely varying arterial pressure. Because the arterial pressure wave modulates pulse pressure, it can result in widely varying systolic and diastolic pressures, diastolic pressure being particularly affected. This case is depicted in FIG. 4. Under these circumstances present oscillometrically based assessment methods can yield widely varying results and systolic/diastolic readings that are significantly inaccurate relative to the ascultatory method. Nor can auscultatory methods easily take arterial pressure wave implications into account because there is no knowledge of breathing frequency, depth, or phase relative to measurement timing.

Present auscultatory and oscillometric techniques share the common shortcoming of not presenting the total picture of arterial pressure. In prior patent Ser. No. 10/932,636, it is asserted and explained that suboptimal breathing is in fact a root cause of hypertension, the reason being that rapid breathing while at rest results in autonomic nervous system acceleration resulting in an increased heartbeat rate, decreased heart rate variability, and increased heart duty cycle. This relationship between breathing and heart rate is depicted in FIG. 5. Yet, the medical community has yet to draw an overt connection between breathing and blood pressure. In part, this is due to the lack of attention paid to respiratory sinus arrhythmia and the resultant "arterial pressure wave" and its relevance to acute and chronic systemic blood pressure. These shortcomings have resulted in the perpetuation of a narrow and erroneous understanding in the medical community as to the root cause of hypertension.

Also, owing to the aforementioned oscillometric assessment limitation, a person that is breathing at the proper rhythm and depth cannot employ present oscillometric measurement devices with confidence, a given device yielding significantly different readings with each measurement as well as different manufacturers yielding significantly different results. This is not because of limitations of oscillometric technology but because the unwritten objective of manufacturers of oscillometric measurement units is consistency between auscultatory and oscillometric assessment of "systolic" and "diastolic" pressures as well as the general lack of recognition of the importance of arterial pressure wave assessment within the industry.

The present state of the art definition of "arterial pressure wave" is the difference between "systolic" and "diastolic" blood pressures. Here again, a lack of recognition exists that that arterial pressure wave varies greatly as a function of respiratory sinus arrhythmia and that the important metric is the amplitude of the arterial pressure wave as a function of breathing.

The foregoing makes clear the fundamental issues and limitations of present auscultatory and oscillometric arterial pressure assessment methods. The present invention addresses these shortcomings by facilitating assessment of arterial pressure taking into account the respiratory sinus arrhythmia induced arterial pressure wave under varying breathing conditions.

SUMMARY OF THE INVENTION

The invention specifies a system and method employing oscillometric measurement methods for purposes of providing a comprehensive characterization of respiratory sinus arrhythmia and consequent arterial pressure wave. Unlike present state of the art blood pressure measurement, the present invention concerns itself with measuring arterial pressure wave amplitude, periodicity, and coherence.

It is important to note that this invention asserts a new way of looking at the matter of arterial pressure. Specified measurement methods and output "metrics" do not equate directly to present state of the art "systolic" and "diastolic" pressures. While the preferred embodiment of the present invention specifies an integrated "blood pressure" measurement capability, other than physical and functional integration, present state of the art oscillometric capability is not of specific interest and assumes present state of the art.

An instructive method is specified for both therapy practitioners and care recipients in the application of the preferred embodiments of the present invention.

BRIEF DESCRIPTION OF THE DRAWING FIGURES

The accompanying drawing figures incorporated in and forming a part of this specification illustrate several aspects of the invention and together with the description serve to explain the principles of the invention.

FIG. 1 depicts the low amplitude heart rate variability signature resulting from typical rapid shallow breathing.

FIG. 2 presents a graphical view of the small variation in arterial pressure wave and resulting small delta in cardiac systole and diastole resulting from relatively rapid shallow breathing.

FIG. 3 depicts the high amplitude heart rate variability signature resulting from slow deep breathing.

FIG. 4 presents a graphical view of the large variation in arterial pressure wave and resulting large delta in cardiac systole and diastole resulting from relatively slow deep breathing.

Figure 8:
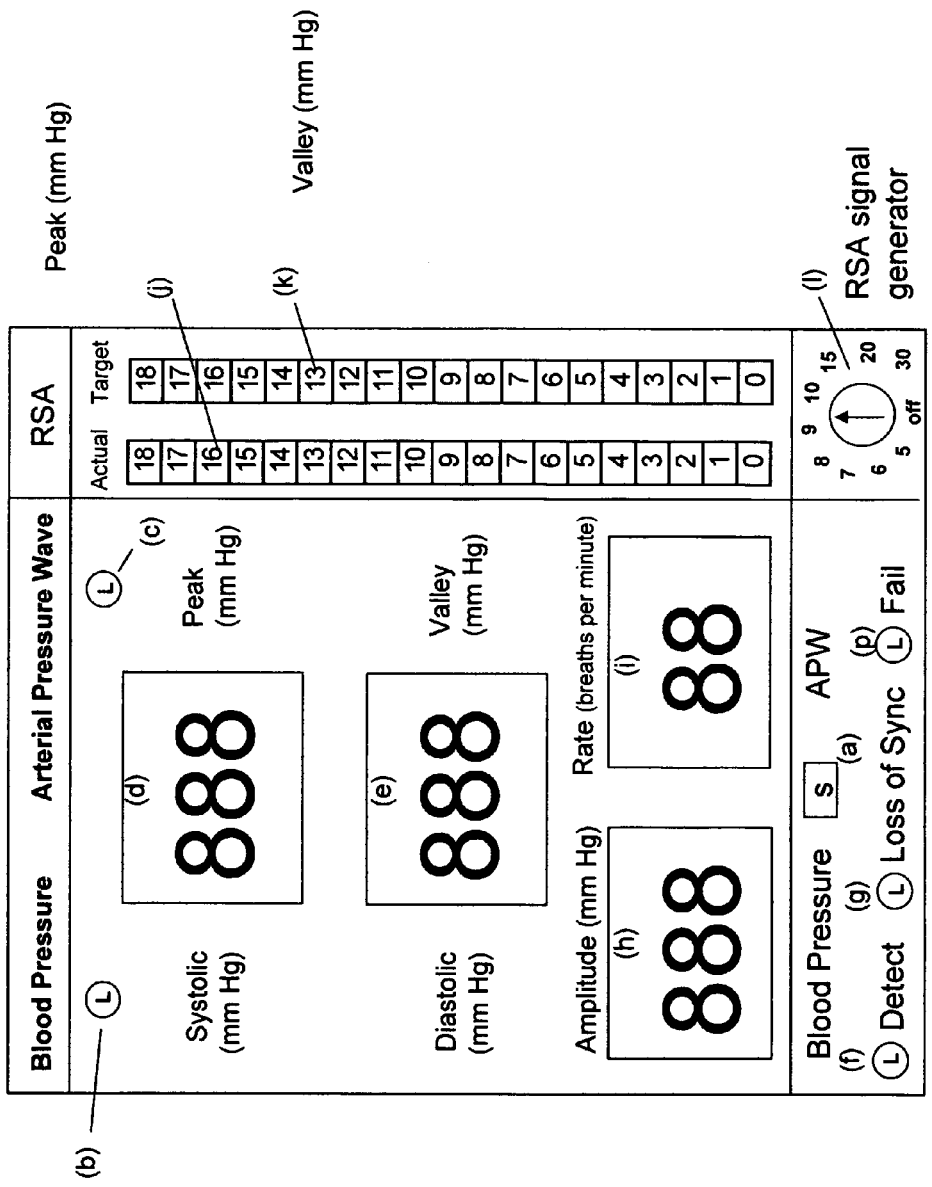

FIG. 8 presents the human machine (HMI) interface and physical positioning of HMI aspects of the preferred embodiment.

Figure 9:
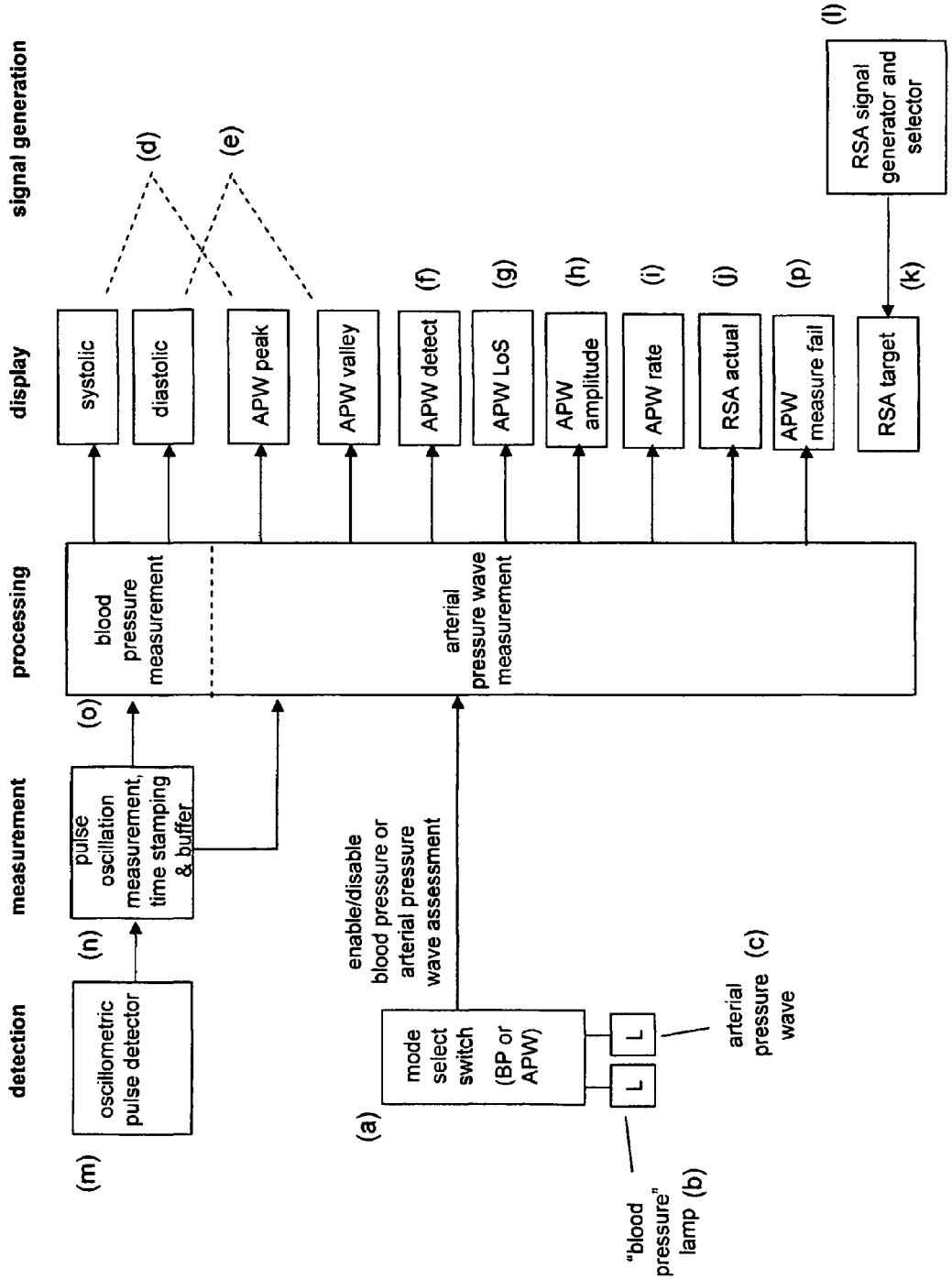

FIG. 9 presents a high level functional block diagram of the preferred embodiment.

Figure 10:
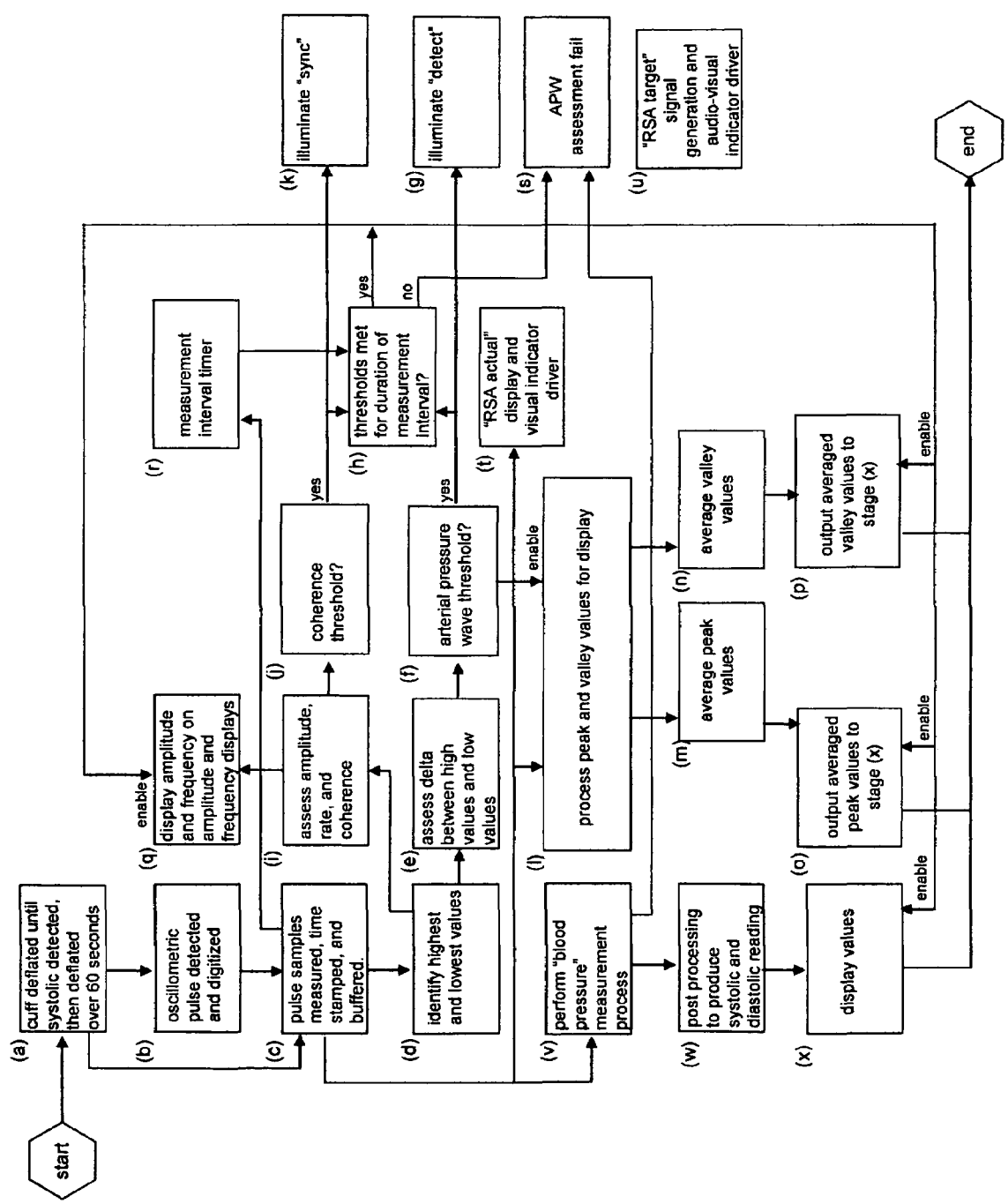

FIG. 10 presents the measurement and control process algorithm.

Figures 11, 12:
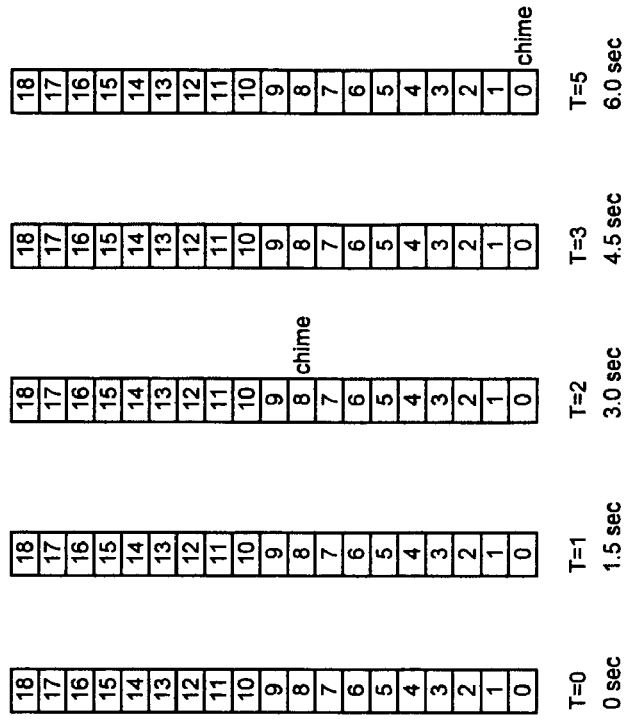

FIG. 11 presents a table defining "RSA signal generator" operation.

FIG. 12 describes the "RSA target" audio visual display.

FIG. 13 presents a table defining "RSA actual" indicator operation.

DETAILED DESCRIPTION OF THE PREFERRED EMBODIMENTS

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

The present invention advances present state by providing arterial pressure wave assessment and characterization.
  a) detecting the presence or absence of an arterial pressure wave,
  b) if an arterial pressure wave is detected, by assessing magnitude and otherwise characterizing amplitude, rate, and coherence.
  c) by facilitating the understanding of the relationship between breathing and arterial pressure wave metrics,
  d) by the application of these value added functions as both a diagnostic and remedial tool for hypertension and related cardiovascular disease.

Figure 1:
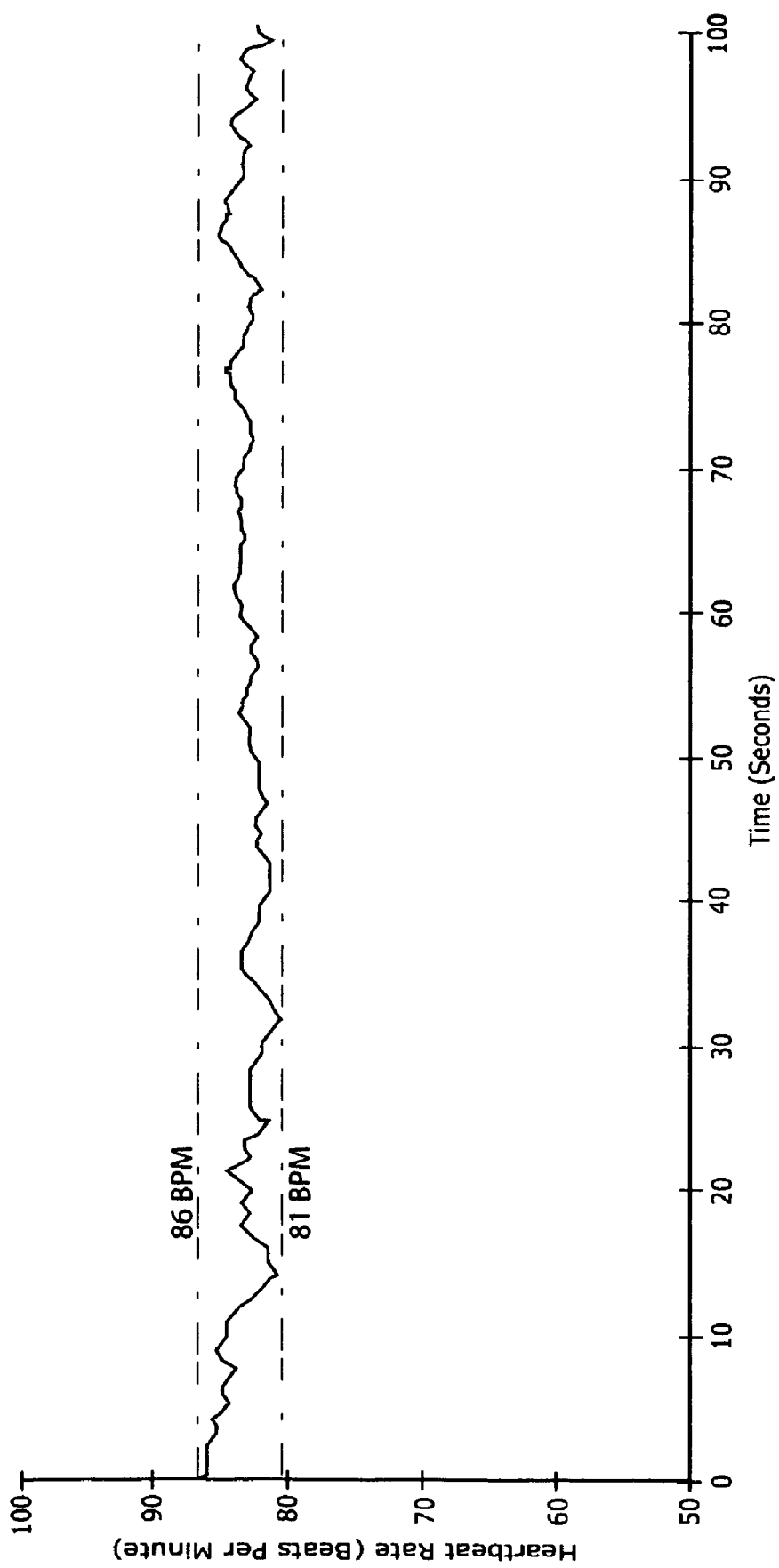
Figure 2:
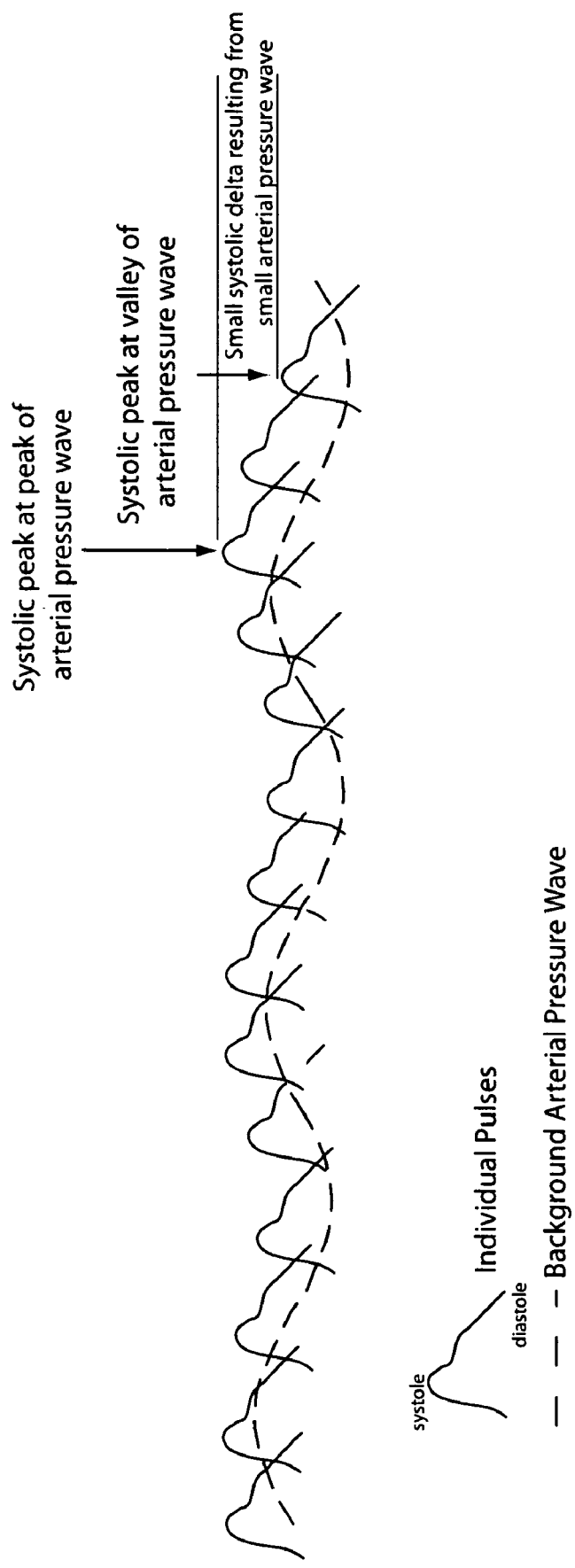
Figure 3:
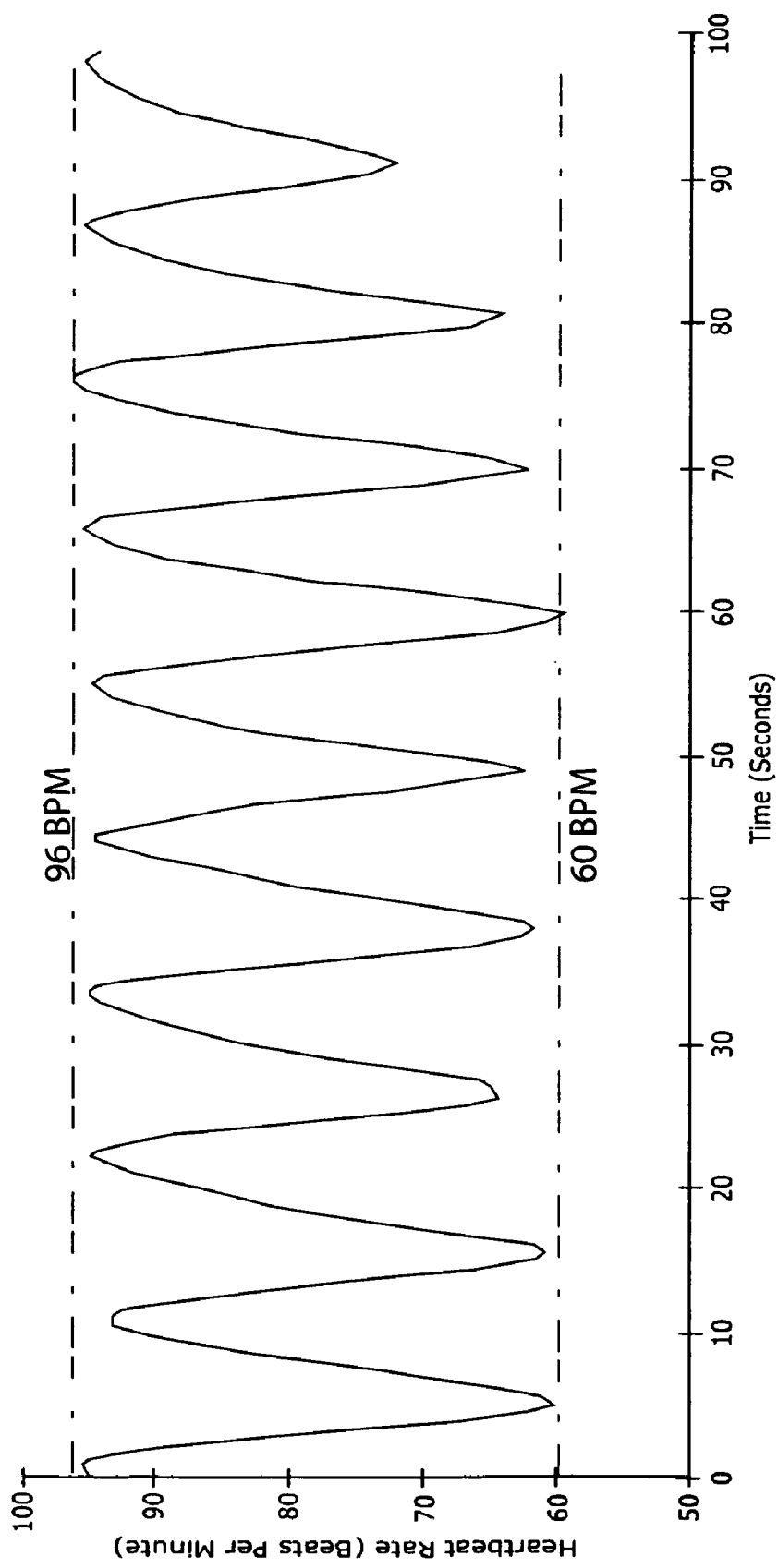
Figure 4:
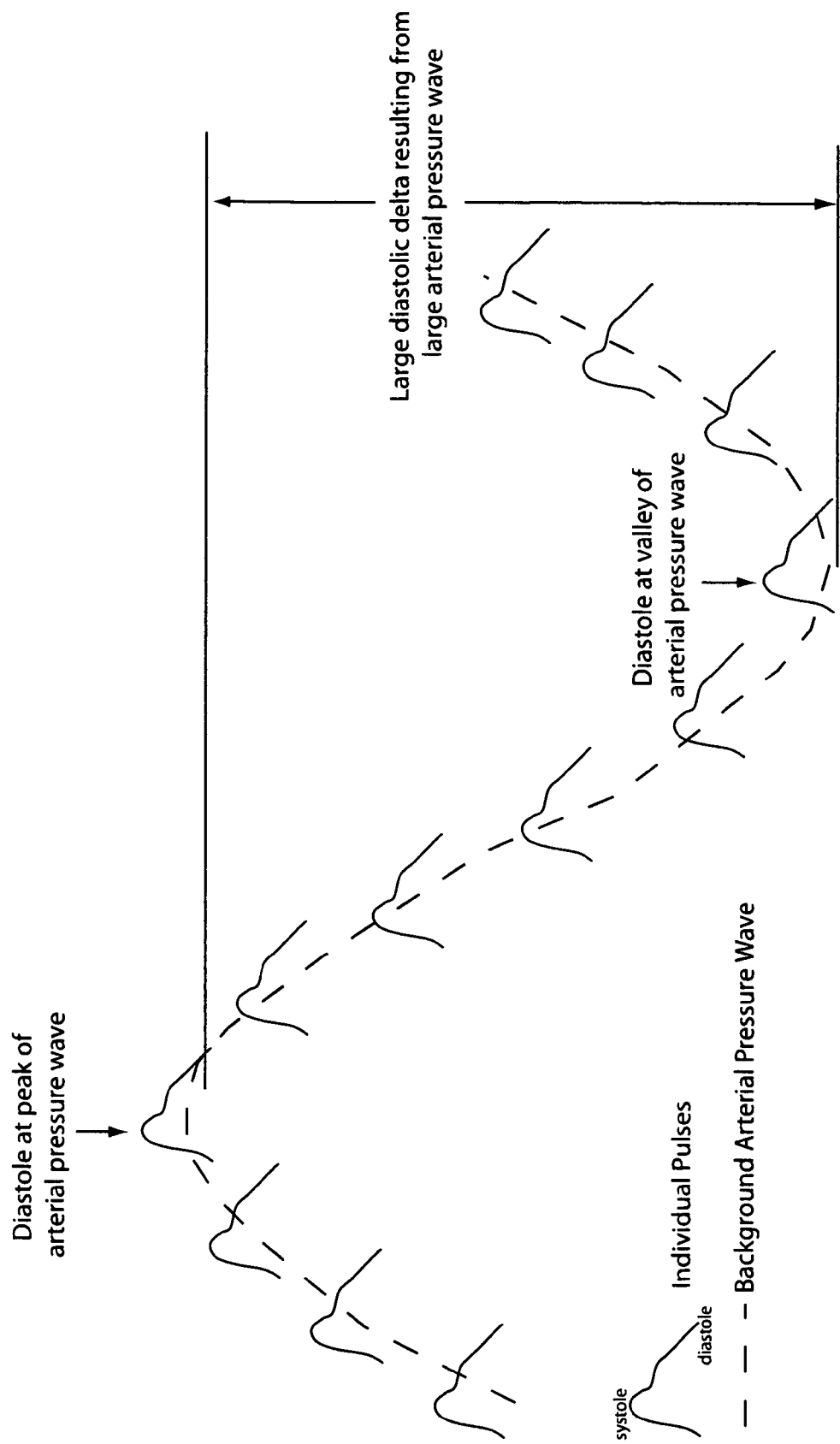
Figure 5:
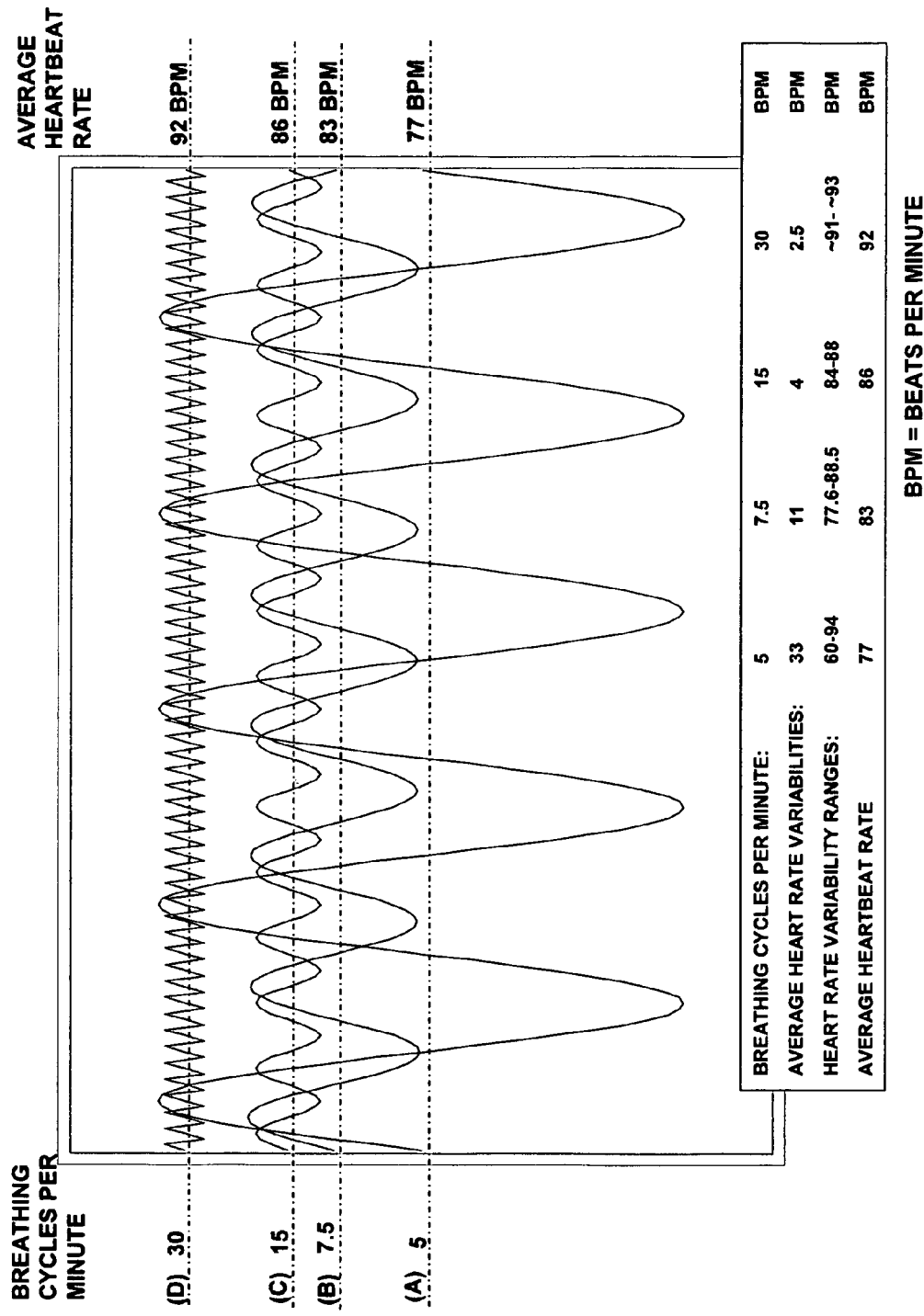
FIG. 5 depicts the basic relationship between breathing frequency and heart rate variability, the arterial pressure wave following the heart beat rate.
Figure 6:
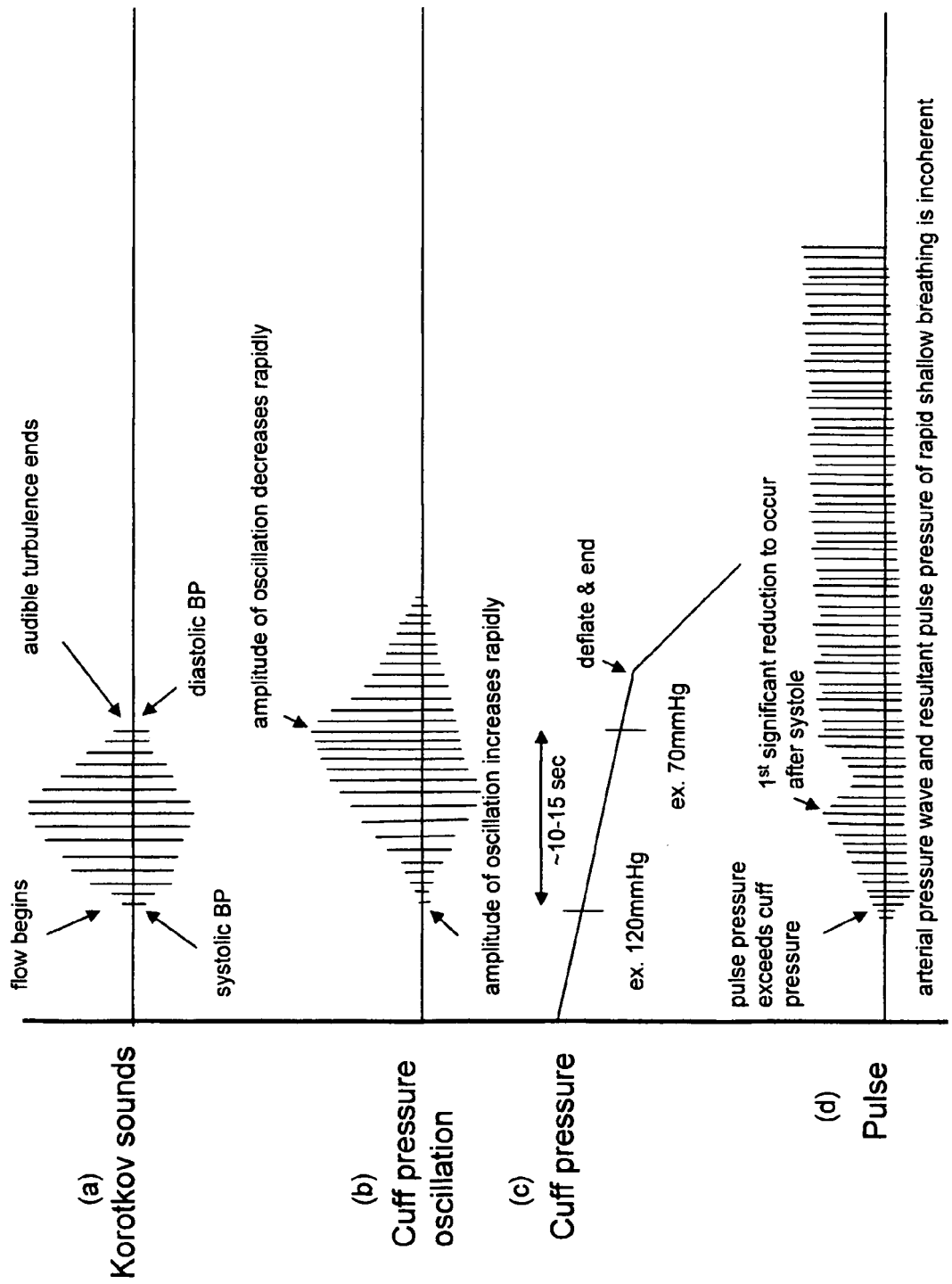
FIG. 6 depicts present state of the art oscillometric systolic and diastolic measurement.
Figure 7:
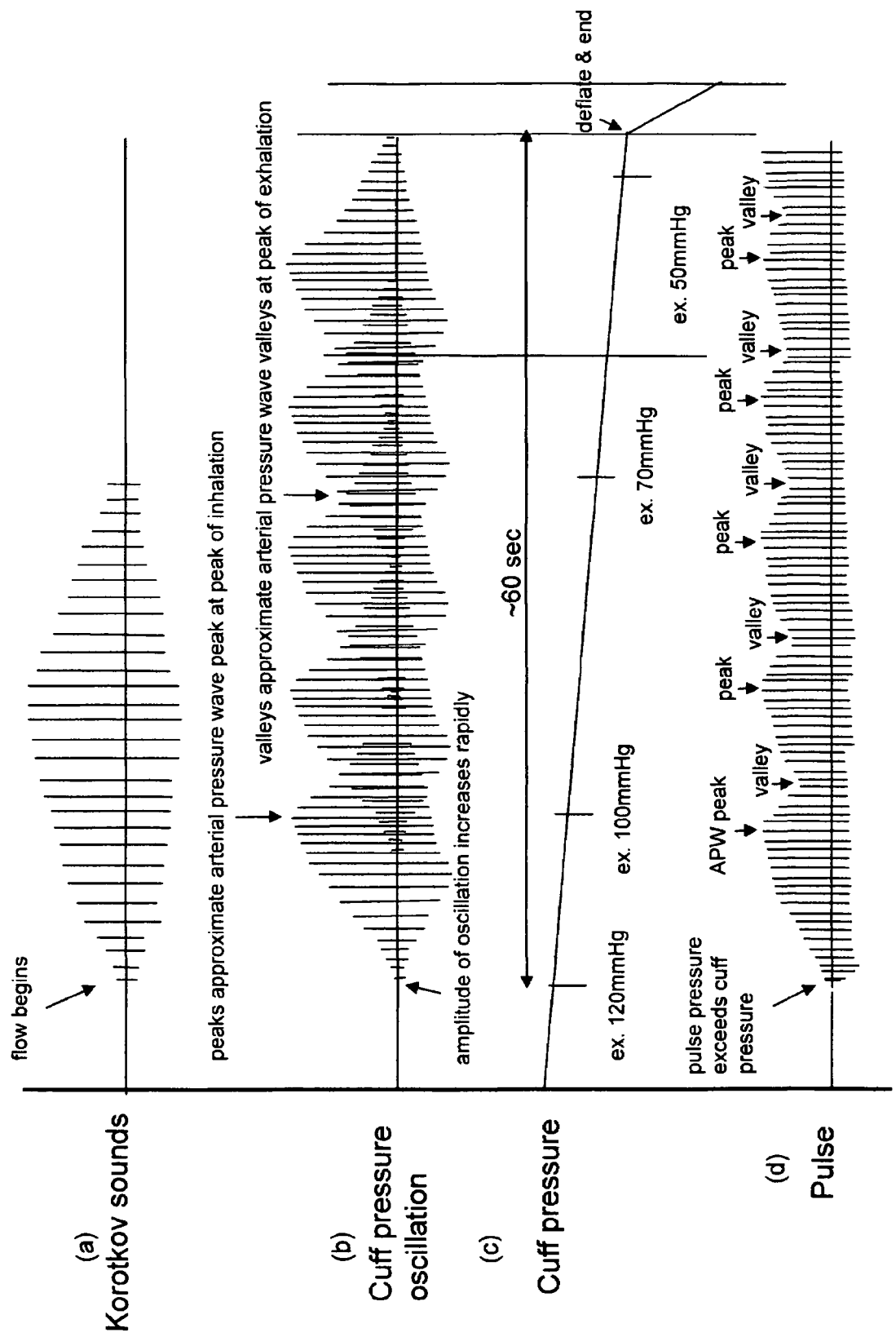
FIG. 7 depicts oscillometric measurement of the arterial pressure wave per the present invention.

With the aid of FIGS. 6-13, the salient features of the preferred embodiment are now explained in detail. The detailed discussion begins with FIG. 6, depicting present state of the art oscillometric blood pressure measurement. Alternatively, FIG. 7 presents oscillometric arterial pressure wave assessment. Blood pressure measurement focuses on determining pressures relating to cardiac systole and diastole. Measurement is performed by monitoring and measuring cuff oscillations as cuff pressure is gradually reduced per FIG. 6(*c*). When blood flow begins on cardiac systole, cuff oscillation promptly begins per FIG. 6(*b*). The amplitude of oscillations increases as pressure is gradually reduced until a moment is reached where amplitude begins to diminish rapidly. This moment corresponds approximately to "diastolic" pressure. Per FIG. 6(*d*) systolic and diastolic assessment occurs on the first systole to exceed cuff pressure and the first "significant" reduction in pulse pressure to occur after the systole event. There is virtually no determinism as to the timing of either systole or diastole relative to respiratory sinus arrhythmia and resulting arterial pressure wave. Again, the reason this works to the degree that it does is that the arterial pressure wave varies to a small degree and is otherwise incoherent and can be therefore be treated as essentially random and nondeterministic for measurement purposes. This is true for most adults while in the state of rest or semi-activity due to relatively rapid shallow breathing.

Alternatively, during arterial pressure wave assessment per the preferred embodiment of the present invention, once oscillation begins, cuff pressure is released very slowly such that oscillation continues for the duration of the measurement as depicted by FIG. 7(c). In this case, oscillation amplitude, as a function of pulse pressure, rises and falls with changes in the arterial pressure wave for the duration of measurement as it reflected by FIG. 7(b). These oscillation amplitude changes are representative of arterial pressure wave peaks and valleys and correspond to increases and decreases in pulse pressure observed during the measurement interval per FIG. 7(d).

While the actual blood pressure measurement cycle typically lasts <10 seconds, arterial pressure wave assessment occurs over the duration of 60 seconds. This 60 second interval accommodates 5 complete breathing cycles of 12 seconds each, the slowest breathing rhythm of concern.

FIG. 8 presents the human machine interface and physical positioning of user displays and controls. The presentation consists of 3 primary sections: "blood pressure", "arterial pressure wave" and "RSA". "Mode switch" (a) selects between conventional oscillometric "blood pressure" assessment and oscillometric "arterial pressure wave" assessment.

When "mode" switch (a) is set to "blood pressure", arterial pressure wave functions are disabled. In blood pressure mode, lamp (b), "blood pressure" is illuminated and lamp (c), "arterial pressure wave" is extinguished. When in blood pressure mode displays (d) and (e) present traditional "systolic" and "diastolic" pressure values in mm Hg. When mode switch (a) is in "arterial pressure wave mode", lamp (c) is illuminated, lamp (b) is extinguished and displays (d) and (e) present values representing arterial pressure wave peaks and valleys respectively, also represented in mmHg.

"Detect lamp" (f) illuminates when an arterial pressure wave of predetermined amplitude is detected and is otherwise extinguished. "Loss of sync" lamp (g) is a function of the coherence of the detected arterial pressure wave. When arterial pressure wave coherence is below threshold, "loss of sync" lamp (g) is illuminated and when above threshold, is extinguished.

Display (h) presents "amplitude" and display (i) presents "rate" of the detected arterial pressure wave. The detected arterial pressure wave drives visual indicator "RSA actual"(j) such that inhalation is reflected in increasing numeric value and exhalation is reflected in decreasing numeric value. The numeric degree to which "RSA actual" display is illuminated is determined by the amplitude of the detected arterial pressure wave. Maximal inhalation illuminates segments 1-18. Maximal exhalation returns the display to "0". "RSA signal generator" (l) is used to provide an audio-visual demonstration of a selected target breathing depth and frequency to which the user may synchronize their breathing during and after the measurement process. This demonstration is presented on display (k). These functions are explained in more detail relative to FIGS. 11, 12, and 13. "Fail" lamp (p) indicates that either blood pressure assessment or the arterial pressure wave assessment "failed". Logic associated with this function is described in the discussion of FIG. 10.

FIG. 9 presents the high level functional block diagram of the preferred embodiment. The system consists of 5 primary functional areas including oscillometric pulse detection, measurement, processing, display, and signal generation functions. As many of these functions have been introduced in the prior discussion, the following discussion of FIG. 9 will focus on aspects yet to be introduced.

"Oscillometric pulse detector" (m) consists of a present state of the art capacitive pressure sensor with analog to digital conversion operating at sampling frequency of 100 samples per second. The digital output of detector (m) is presented to "pulse oscillation measurement, time stamp, and buffer" function (n) where digital samples are assigned a serial number, assigned a pressure value, time stamped, and buffered. The processed output is presented to the processing function which is enabled to perform either "blood pressure measurement" or "arterial pressure wave measurement" depending on the position of mode switch (a). When mode switch (a) is in "blood pressure" mode, traditional oscillometric blood pressure measurement is performed and the results presented on displays (d) and (e) representing "systolic" and "diastolic" values, respectively. When the mode switch is set to "arterial pressure wave", the processing function performs arterial pressure wave measurement and the results are presented on displays (d) and (e) which double to present both blood pressure and arterial pressure wave measurement values.

"Arterial pressure wave" mode having been selected, samples are transferred from "pulse oscillation measurement, time stamping, and buffer" function (n) to processing function (o) which processes samples for purposes of assessing the presence, magnitude, and periodicity of an arterial pressure wave, the objective being the accurate characterization of the pressure wave, if existent. Because the output of "pulse oscillation measurement, time stamping, and buffer" function (n) consists of time stamped pressure values, all measurement analysis and processing occurs in the time domain eliminating any requirement for digital signal processing and Fourier transformation.

The processed output of processing function "(o)" is ultimately presented to the user on displays "APW peak" (d) through "APW fail" (p). A detailed discussion of the logical process associated with "arterial pressure wave" measurement is the focus of FIG. 10, discussion of which will now commence.

The measurement and control process algorithm of FIG. 10 consists of stages (a) through (x). The process begins with cuff inflation (a). Per prior discussion of FIG. 7, unlike present state of the art oscillometric blood pressure assessment, the present invention inflates the cuff and then releases pressure until the systolic pressure is detected. Once systolic pressure is detected and cuff oscillations begin, deflation continues for 60 seconds. This is to accommodate 5 arterial pressure wave cycles of 12 seconds each, the slowest breathing rhythm of interest. The output of stage (a) is passed to stage (b) where oscillations are detected and digitized at a 10 millisecond rate. Digitized samples are passed to stage (c) where they are assigned a pressure, time stamped, and buffered. Cuff pressure is passed from stage (a) to stage (c) for purposes of correlating oscillometric samples with cuff pressure over time, this being required for purposes of attributing a pressure value to pulse samples of varying amplitude. The output of stage (c) is passed to stage (d) where highest and lowest measured values are determined, these being representative of arterial pressure wave peaks and valleys occurring during the 60 second measurement interval.

The output of stage (d) is presented to stage (e) wherein the delta between highest and lowest samples is assessed. This delta is presented to stage (f) where it is compared against a predetermined threshold. If the threshold is exceeded, the "detect" lamp (g) is illuminated. The output of stage (f) is also presented to logic function (h) where it forms a part of the criteria for enabling the output display of the arterial pressure wave measurement process.

The output of process stage (d) is concurrently passed to stage (i) where highest and lowest samples are processed to determine, rate, periodicity and coherence thereof. The coherence value is passed from stage (i) to stage (j) where it is compared against a pre-established threshold. If the threshold is exceeded, the "sync" lamp (k) is extinguished and is otherwise illuminated. The output of stage (j) is also presented to logic function (h) where it forms a part of the criteria for enabling the output display of the arterial pressure wave measurement process.

The output of stage (f) is concurrently presented to stage (l) where it enables the post processing of all measured time stamped and buffered samples to determine arterial pressure wave peak and valley pressure values, timing and amplitude ranges for peaks and valleys having already been determined. This function having been performed, stage (m) averages values relating to arterial pressure wave peaks. Similarly, stage (n) averages values relating to arterial pressure wave valleys. Averaged values pertaining to arterial pressure wave peaks and valleys are output to respective displays via output stages (o) and (p) respectively.

Stage (i) determines arterial pressure wave amplitude and rate across the measurement interval. The output of stage (i) is presented to stage (q) for presentation on "amplitude" and "rate" displays. Amplitude is presented in mmHg and rate is presented in "cycles per minute".

The moment of oscillation detection is passed from stage (c) to measurement interval timing stage (r) where it initiates the beginning of the 60 second measurement interval. The output of stage (r) is passed to logic function (h) where it along with the "coherence" threshold of stage (j), and the "detect" threshold of stage (f) form the criteria for arterial pressure wave measurement "success", the output of stage (h) enabling the display of arterial pressure wave assessment. If thresholds are not maintained for the 60 second duration, stage (i) signals stage (s) that the assessment "failed" lighting the "fail" lamp on the human machine interface.

Stages (t) and (u) support "RSA actual" and "RSA target" functions, respectively.

Stage (u) is an independent process providing the manual selection of a "target" RSA frequency. This function presents both an audible and visual representation of target breathing frequency and consequent depth as selected. Depending on the setting, the "RSA target" audiovisual indicator (k) of FIGS. 8 and 9, is illuminated. The numeric value is a function of breathing frequency. This function can be employed by the user as a "breathing reference" to which their "RSA actual" ((j) of FIGS. 8 and 9) can be compared during measurement. It also serves to synchronize the breathing of the user such that their arterial pressure wave is maximally coherent and therefore easily and accurately assessed. This function is further explained in FIGS. 11 and 12.

Stage (t) accepts measured values from stage (c) and uses this information to generate a sequential signal that drives the "RSA actual" indicator such that the amplitude and phase of the arterial pressure wave is visually represented, this being a function of respiratory sinus arrhythmia. Maximal inhalation illuminates segments 1-18. Maximal exhalation returns the display to "0". The displayed numeric value is dependent on amplitude, rate, and phase of the arterial pressure wave. Values relating to this process are specified in the table of FIG. 13.

Lastly, depending on "mode" of operation, values representing the result of either "blood pressure" or "arterial pressure wave" assessment are displayed. If "blood pressure" assessment is performed, measured and stamped samples along with corresponding cuff pressures are passed from stage (c) to stage (v) where the "systolic" and "diastolic" measurement process is performed. Results are passed to stage (w) for post processing and ultimately to display stage (x).

FIG. 11 presents a table specifying the "RSA Signal Generator" function. The range of settings in "breathing cycles per minute" is presented along with related frequency of oscillation and visual numeric values. Only even numeric values are specified for brevity.

FIG. 12 presents a view of "target RSA" audiovisual indicator demonstrating the cyclic nature of the display. It presents the display at 5 different times as it cycles to present a breathing cycle of 10 cycles per second (10 cycles per minute also highlighted in FIG. 11), 10 cycles per minute being used as an example. An audible chime sounds when the display reaches uppermost and lowermost moments.

FIG. 13 presents a table defining the operation of the "RSA actual" visual indicator relating input arterial pressures with visual display outputs. "RSA target" visual indicator values of tables 11 and 13 are correlated such that both "RSA actual" and "RSA target" visual displays will indicate approximately the same values when a user breathes in synchrony with the "RSA signal generator".

This concludes the system description. Both hardware-optimized and software-optimized topologies are assumed within the scope of the present invention as well as discrete vs. integrated implementations including integration with other medical or non-medical present or future products and/or systems.

In summary, these features of the present invention provide the following value added utility to a care practitioner or user:

a) "An integrated" blood pressure and arterial pressure measurement capability" such that the same physical unit can be employed to assess both "blood pressure" and "arterial pressure wave assessment".

b) Is there a detectable arterial pressure wave? If no, it means that the patient or user is not breathing adequately. If suffering from elevated blood pressure suboptimal breathing may be the root cause and breathing therapy may be indicated.

c) If there is an arterial pressure wave, what is the amplitude? If a wave exists but is of low amplitude it means that the patient/user is not breathing with sufficient depth, again potentially elevating blood pressure and once again, breathing therapy may be indicated.

d) If an arterial pressure wave exists, what is the rate? A relatively high frequency means that the patient/user is breathing too rapidly, and as a consequence, with insufficient depth. Again, hypertension may be rooted in this breathing pattern and breathing therapy may be indicated.

e) Because breathing depth strongly influences diastolic pressure, a low amplitude arterial pressure wave, implies elevated diastolic pressure. Consequently, arterial pressure wave analysis can be used to aid in the diagnosis and treatment of elevated diastolic pressure.

f) Via the visual display of the changing arterial pressure wave, the care recipient can easily comprehend and understand the mechanics of how breathing affects arterial pressure.

g) "RSA actual" can be compared in real time to "RSA target" such that proper breathing frequency and depth can be reinforced.

h) The "RSA signal generator" can be used for independent breathing training whether or not a measurement is being performed. This training is for the purpose of reinforcing proper breathing habits on an ongoing basis.

Instructive Method for Employing and Applying Preferred Embodiments

The care recipient is engaged and otherwise instructed in the following instructive method. A careful overview of care recipients health status and background are conducted.
1. The care recipient's blood pressure is assessed using the "blood pressure" measurement function.
2. If the care recipient exhibits hypertensive or marginal systolic or diastolic pressure, the present invention is placed in "arterial pressure wave" assessment mode and arterial pressure wave assessment commences.
3. The "RSA actual" visual indicator is indicative of care recipient breathing status during measurement, a low indication indicating suboptimal breathing depth and frequency and a high indication indicating optimal depth and frequency.
4. "Detect" and "loss of sync" lamps also indicate the status of care recipient's arterial pressure wave. If the unit fails to "detect" the presence of an arterial pressure wave for the duration of measurement, it is immediately indicative that breathing status is suboptimal and that breathing therapy may in order.
5. The care recipient is not asked to correct their breathing during the first assessment because a momentary change in breathing will result in a reading that is not representative of the care recipient's normal breathing status.
6. If the arterial pressure wave assessment process fails, it is indicative that the arterial pressure wave is either insufficient to be detected accurately or lacks coherence to the extent that it cannot be adequately assessed.
7. In the case of #6, a second assessment is undertaken and the care recipient is requested to pay close attention to the RSA actual indicator as they inhale and exhale deeply and rhythmically. By doing this, the care recipient understands the connection between breathing and arterial pressure wave assessment and ultimately their systolic and diastolic pressure values.
8. The care recipient is then instructed in the use of the RSA signal generator and related RSA target audio-visual display.
9. The recommendation is made that the care recipient use the RSA signal generator to practice breathing at progressively lower and lower rates until they can comfortably breathe at a rate approaching 5 breaths per minute.
10. The care recipient's systolic and diastolic pressures are assessed regularly using the "blood pressure" function of the present invention.
11. The care recipient is instructed to continue lowering their blood pressure through the continued reduction in breathing frequency until healthy systolic and diastolic readings result.
12. The care recipient is instructed to continue to breathe at a relatively slow deep rhythm as life circumstances permit on an ongoing basis.
13. The care recipient is instructed in to cultivate through practice, these objectives and recommendations:
    a. a high arterial pressure wave amplitude >40 mm Hg. as presented on "amplitude" display (h) of FIGS. 8 and 9.
    b. an "RSA actual" as depicted on display (j) of FIGS. 8 and 9 in excess of numeric value "12".
    c. an arterial pressure wave "rate" as presented on display (i) of FIGS. 8 and 9 approaching 5 cycles per minute,
    d. a relatively low arterial pressure wave "valley" value (<70 mm Hg.) as presented on display (e) of FIGS. 8 and 9.

This concludes the discussion of the instructive method.

Those skilled in the art will recognize improvements and modifications to the preferred embodiments of the present invention. All such improvements and modifications are considered within the scope of the concepts disclosed herein and the claims that follow.

What is claimed:

1. A method for assessing breathing optimality of a patient comprising:
    measuring a varying breathing induced arterial pressure wave of a patient;
    assessing optimality of a breathing process of the patient based on the measured arterial pressure wave; and
    providing a characterization to the patient of the optimality of the patient's breathing process based on the measured arterial pressure wave.

2. The method of claim 1 wherein measuring the varying breathing induced arterial pressure wave of the patient comprises measuring a varying pulse pressure of the patient via oscillometry.

3. The method of claim 1 wherein measuring the varying breathing induced arterial pressure wave of the patient comprises measuring one or more from the group consisting of a pulse pressure amplitude of the patient, pulse pressure periodicity of the patient, and coherence of the patient.

4. The method of claim 1 wherein measuring the varying breathing induced arterial pressure wave of the patient comprises measuring oscillometric characteristics of the arterial pressure wave of the patient over a measurement interval including multiple breathing cycles; and
    wherein assessing optimality of a breathing process of the patient based on the measured arterial pressure wave comprises assessing changes in the arterial pressure wave pressure of the patient over the measurement interval using the oscillometric characteristics.

5. The method of claim 1 wherein assessing the optimality of a breathing process of the patient is performed for an approximate 60 second period defining an arterial pressure wave assessment cycle and further comprises:
    sustaining a pulse oscillation for the approximate 60 second period by gradually reducing a cuff pressure; and
    measuring multiple arterial pressure wave cycles of the patient during the arterial pressure wave assessment cycle.

6. The method of claim 1 wherein measuring the varying breathing induced arterial pressure wave of the patient further comprises
    detecting cardiac systole of the patient; and
    detecting pulse oscillations of the patient corresponding to the cardiac systole occurring at the peak of the breathing induced arterial pressure wave.

7. The method of claim 1 wherein measuring the varying breathing induced arterial pressure wave of the patient comprises:
    measuring an oscillometric pulse oscillation amplitude of the patient; and
    measuring an arterial pressure wave amplitude of the patient as a function of the measured oscillometric pulse oscillation amplitude of the patient, and
    wherein providing a characterization to the patient of the optimality of the patient's breathing process based on the measured arterial pressure wave comprises displaying the arterial pressure wave amplitude of the patient on a display for diagnostic and remedial purposes.

8. The method of claim 1 wherein measuring the varying breathing induced arterial pressure wave of the patient comprises:

measuring an oscillometric pulse oscillation periodicity of the patient; and measuring an arterial pressure wave rate of the patient as a function of the oscillometric pulse oscillation periodicity, and wherein providing a characterization to the patient of the optimality of the patient's breathing process based on the measured arterial pressure wave comprises displaying the arterial pressure wave rate of the patient on a display for diagnostic and remedial purposes.

9. The method of claim 1 wherein measuring the varying breathing induced arterial pressure wave of the patient comprises:

measuring an oscillometric pulse oscillation amplitude of the patient;

measuring an actual variation in arterial pressure wave amplitude representative of changes in arterial pressure wave pressure of the patient as a function of changes in the oscillometric pulse oscillation amplitude of the patient; and wherein providing a characterization to the patient of the optimality of the patient's breathing process based on the measured arterial pressure wave comprises displaying the actual variation in arterial pressure wave amplitude for the patient for diagnostic and remedial purposes.

10. The method of claim 1 wherein measuring the varying breathing induced arterial pressure wave of the patient further comprises:

detecting cardiac diastole of the patient; and detecting pulse oscillations of the patient corresponding to the cardiac diastole occurring at the valley of the breathing induced arterial pressure wave.

11. The method of claim 1 wherein providing a characterization to the patient of the optimality of the patient's breathing process based on the measured arterial pressure wave comprises displaying measured values associated with the varying breathing induced arterial pressure wave on a display.

12. The method of claim 1 further comprising instructing the patient on a breathing cycle based on the characterization to the patient of the optimality of the patient's breathing process based on the measured arterial pressure wave.

13. The method of claim 12 wherein instructing the patient on a breathing cycle based on the characterization to the patient of the optimality of the patient's breathing process based on the measured arterial pressure wave comprises generating target breathing frequencies of 5, 6, 7, 8, 9, 10, 15, 20, and 30 breathing cycles per minute to instruct the patient on how to synchronize their breathing cycle with the target breathing frequency.

14. The method of claim 12 wherein instructing the patient on a breathing cycle based on the characterization to the patient of the optimality of the patient's breathing process based on the measured arterial pressure wave comprises providing an audible chime to the patient that sounds at a peak of desired inhalation and at a peak of desired exhalation.

15. The method of claim 12 wherein instructing the patient on a breathing cycle based on the characterization to the patient of the optimality of the patient's breathing process based on the measured arterial pressure wave comprises:

providing a target breathing frequency and an actual breathing frequency of the patient on a display; and providing an output to the patient such that the target breathing frequency and actual breathing frequency of the patient are correlated to each other to facilitate the patient breathing in synchrony with the target breathing frequency to bring the actual breathing frequency of the patient into amplitude and time alignment with the target breathing frequency.

16. The method of claim 12 wherein instructing the patient on a breathing cycle based on the characterization to the patient of the optimality of the patient's breathing process based on the measured arterial pressure wave comprises:

providing a target breathing reference to the patient; and instructing the patient to breathe to increase an amplitude of the varying breathing induced arterial pressure wave of the patient to match an amplitude of the target breathing reference.

17. A system for assessing breathing optimality of a patient comprising:

a display module for providing information to a patient;

an oscillometric pulse detector adapted to determine an oscillometric pulse of the patient; and a processing module adapted to:

measure a varying breathing induced arterial pressure wave of the patient based upon the oscillometric pulse;

assess optimality of a breathing process of the patient based on the measured arterial pressure wave; and provide a characterization to the patient of the optimality of the patient's breathing process based on the measured arterial pressure wave.

18. The system of claim 17 wherein the processing module is adapted to measure the varying breathing induced arterial pressure wave of the patient based upon the oscillometric pulse by being adapted to measure a varying pulse pressure of the patient based upon the oscillometric pulse.

19. The system of claim 17 wherein the processing module is further adapted to measure the varying breathing induced arterial pressure wave of the patient based upon the oscillometric pulse by one of the group consisting of a pulse pressure amplitude of the patient, a pulse pressure periodicity, and a coherence of the patient.

20. The system of claim 17 wherein the processing module is further adapted to measure the varying breathing induced arterial pressure wave of the patient based upon the oscillometric pulse by being adapted to measure oscillometric characteristics of the varying breathing induced arterial pressure wave over a measurement interval including multiple breathing cycles and assessing pressure changes in the varying breathing induced arterial pressure wave over the measurement interval using the oscillometric characteristics.

21. The system of claim 17 wherein the processing module is further adapted to assess optimality of a breathing process of the patient based on the measured arterial pressure wave by being adapted to:

sustain a pulse oscillation for an approximate 60 second period defining an arterial pressure wave assessment cycle by gradually reducing cuff pressure; and measure multiple arterial pressure wave cycles during the arterial pressure wave assessment cycle.

22. The system of claim 17 wherein the processing module is further adapted to measure the varying breathing induced arterial pressure wave of the patient based upon the oscillometric pulse by being adapted to detect cardiac systole and to detect pulse oscillations corresponding to the cardiac systole of the patient occurring at the peak of the breathing induced arterial pressure wave.

23. The system of claim 17 wherein the processing module is further adapted to measure a varying breathing induced arterial pressure wave of the patient based upon the oscillometric pulse by being adapted to:

measure an oscillometric pulse oscillation amplitude based upon the oscillometric pulse of the patient;

measure an arterial pressure wave amplitude as a function of the oscillometric pulse oscillation amplitude; and wherein the processing module is further adapted to display the arterial pressure wave amplitude of the patient for diagnostic and remedial purposes on the display module.

24. The system of claim 17 wherein the processing module is further adapted to measure a varying breathing induced arterial pressure wave of the patient based upon the oscillometric pulse by being adapted to:

measure an oscillometric pulse oscillation periodicity based upon the oscillometric pulse;

measure an arterial pressure wave rate as a function of the oscillometric pulse oscillation periodicity; and wherein the processing module is further adapted to display the arterial pressure wave rate of the patient for diagnostic and remedial purposes on the display module.

25. The system of claim 17 wherein the processing module is further adapted to measure a varying breathing induced arterial pressure wave of the patient based upon the oscillometric pulse by being adapted to:

measure an oscillometric pulse oscillation amplitude based upon the oscillometric pulse;

measure an actual breathing induced amplitude variation representative of changes in arterial pressure wave pressure as a function of changes in the oscillometric pulse oscillation amplitude; and wherein the processing module is further adapted to display the actual breathing induced amplitude variation of the patient for diagnostic and remedial purposes on the display module.

26. The system of claim 17 wherein the processing module is further adapted to instruct the patient on a breathing cycle based on the characterization to the patient of the optimality of the patient's breathing process based on the measured arterial pressure wave.

27. The system of claim 26 wherein the processing module is adapted to instruct the patient on a breathing cycle based on the characterization to the patient of the optimality of the patients breathing process based on the measured arterial pressure wave by being adapted to provide a target breathing reference to the patient; and instructing the patient to breathe to increase an amplitude of the varying breathing induced arterial pressure wave of the patient to match an amplitude of the target breathing reference.

28. The system of claim 15 wherein the processing module is adapted to instruct the patient on a breathing cycle based on the characterization to the patient of the optimality of the patient's breathing process based on the measured arterial pressure wave by being adapted to provide an audible chime to the patient that sounds at a peak of desired inhalation and at a peak of desired exhalation.

29. The system of claim 15 wherein the processing module is adapted to instruct the patient on a breathing cycle based on the characterization to the patient of the optimality of the patient's breathing process based on the measured arterial pressure wave by being adapted to provide a target breathing induced arterial pressure wave amplitude and an actual breathing induced arterial pressure wave amplitude of the patient on a display; and is further adapted to provide an output to the patient such that the target breathing induced arterial pressure wave amplitude and actual breathing induced arterial pressure wave amplitude of the patient are correlated to each other to facilitate the patient breathing in synchrony with the target breathing frequency to bring the actual breathing induced arterial pressure wave of the patient into amplitude and time alignment with the target arterial pressure wave amplitude.

30. The system of claim 17 wherein the processing module is adapted to measure the varying breathing induced arterial pressure wave of the patient by being adapted to:

detect cardiac diastole of the patient; and detect pulse oscillations of the patient corresponding to the cardiac diastole occurring at the valley of the breathing induced arterial pressure wave.

\* \* \* \* \*

UNITED STATES PATENT AND TRADEMARK OFFICE
CERTIFICATE OF CORRECTION

PATENT NO.         : 7,458,937 B2                                                Page 1 of 1
APPLICATION NO.  : 11/032662
DATED              : December 2, 2008
INVENTOR(S)       : Stephen Bennett Elliott It is certified that error appears in the above-identified patent and that said Letters Patent is hereby corrected as shown below:

Column 14, line 4: change "patients" to "patient's"

Signed and Sealed this

Sixth Day of January, 2009

JON W. DUDAS
*Director of the United States Patent and Trademark Office*